United States Patent [19]

Waldmann et al.

[11] 3,974,224
[45] Aug. 10, 1976

[54] PROCESS FOR PREPARING ALDEHYDES FROM OXIRANE COMPOUNDS

[75] Inventors: Helmut Waldmann, Leverkusen; Wulf Schwerdtel, Leverkusen-Steinbuechel; Wolfgang Swodenk, Odenthal-Gloebusch, all of Germany

[73] Assignee: Bayer Aktiengesellschaft, Leverkusen, Germany

[22] Filed: Oct. 25, 1973

[21] Appl. No.: 409,544

[30] Foreign Application Priority Data
Oct. 27, 1972    Germany............................ 2252719

[52] U.S. Cl............................ 260/601 R; 260/465 F; 260/465 G; 260/465 R; 260/465.1; 260/465.6; 260/465.7; 260/598; 260/599; 260/600 R; 260/601 H

[51] Int. Cl.$^2$................... C07C 47/02; C07C 47/52; C07C 47/56; C07C 121/58

[58] Field of Search........ 260/601 R, 601 H, 600 R, 260/599, 598, 465 R, 465 F, 465 G, 465.1, 465.6, 465.7

[56] References Cited
UNITED STATES PATENTS
2,694,090    11/1954    Wild et al. ...................... 260/601 R

*Primary Examiner*—Alton D. Rollins
*Assistant Examiner*—D. B. Springer
*Attorney, Agent, or Firm*—Burgess, Dinklage & Sprung

[57] ABSTRACT

Aldehydes are prepared by reacting an oxirane compound with hydrogen peroxide in the presence of a boron compound.

8 Claims, No Drawings

PROCESS FOR PREPARING ALDEHYDES FROM OXIRANE COMPOUNDS

BACKGROUND

This invention relates to a process for the production of aldehydes from oxirane compounds and hydrogen peroxide.

Aldehydes are important intermediate products for the synthesis of medicaments or azo dyes. Also certain aldehydes, for example glutardialdehydes, are used, as tanning agents.

It is known that aldehydes can be obtained by a two-stage process in the first stage of which certain oxirane compounds are converted into the corresponding 1,2-diols which are subsequently converted in the second stage into the corresponding aldehydes by reaction with compounds such as lead tetra-acetate (R. Criegee, Ber. d. dtsch. chem. Ges. 64, 264 (1931)) or periodic acid (L. Malaprade, Bull. Soc. Chim. France (4) 43, 683 (1928)).

One disadvantage of this process is that the 1,2-diols must be prepared as intermediate products. Another disadvantage is that the oxidising agents used in the second stage, such as lead tetra-acetate or periodic acid, do not have a catalytic effect upon the reaction, instead they actually take part in it. Thus, the conversion products of the oxidising agents used for splitting the 1,2-diols have to be isolated on completion of the reaction and converted into the corresponding oxidising starting compounds before they are reused.

SUMMARY

It has now been found that aldehydes can be obtained from oxirane compounds by reaction with hydrogen peroxide, providing reaction of the oxirane compound with hydrogen peroxide is carried out in the presence of a boron compound.

DESCRIPTION

Oxirane compounds suitable for use in the process according to the invention are compounds corresponding to the general formula (I):

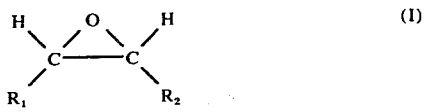

in which $R_1$ and $R_2$ independently of one another represent hydrogen; a phenyl group optionally substituted by fluorine, chlorine, cyanide, $C_1$–$C_6$-alkoxy, $C_1$–$C_3$-alkyl, or oxiranyl; a linear or branched $C_1$–$C_{12}$-alkyl radical optionally substituted by fluorine, chlorine, OH, $C_1$–$C_6$-alkoxy, carbo-$C_1$–$C_3$-alkoxy cyanide, phenyl or oxiranyl; a $C_5$–$C_7$-cycloalkyl radical optionally substituted by fluorine, chlorine, hydroxy, $C_1$–$C_6$-alkyl, $C_1$–$C_6$-alkoxy, carbo-$C_1$–$C_3$-alkoxy, phenyl or oxiranyl; in addition to which the radicals $R_1$ and $R_2$ together with the carbon atoms of the oxirane ring may represent a carbocyclic ring having up to 24 carbon atoms optionally substituted by fluorine, chlorine, hydroxy, $C_1$–$C_3$-alkyl, phenyl, $C_1$–$C_6$-alkoxy, carbo-$C_1$–$C_3$-alkoxy or cyanide.

The following are examples of substituted phenyl groups: 4-chlorophenyl, 2,4-dichlorophenyl, 4-methoxyphenyl, 4-chloro-2-methoxyphenyl, 4-propoxyphenyl, 4-tert.-butoxyphenyl, 4-n-hexoxyphenyl, 4-cyanophenyl and 4-cyano-3,5-dimethylphenyl.

The following are mentioned as examples of linear or branched $C_1$–$C_{12}$-alkyl radicals: methyl, ethyl, propyl, n-butyl, isobutyl, tert.-butyl, pentyl, hexyl, heptyl, octyl, nonyl, decyl, undecyl, dodecyl, pentadecyl, hexadecyl, octadecyl, and their isomers. $C_2$–$C_6$-alkyl radicals are preferably used.

The following are mentioned as examples of susbstituted alkyl radicals: chloromethyl, β-chloroethyl, β-ethyl hexyl, isopropyl, 2-hydroxymethylhexyl, β-methoxyethyl, 3-propoxypropyl, n-hexoxy-methyl, 2,4,6-trimethoxyhexyl, 2-(methoxymethyl)-propyl, (carbomethoxy)-methyl, 3-(carbopropoxy)-propyl, 3-(carbomethoxy)-hexyl, 3-(β-carbomethoxyethyl)-butyl, β-cyanoethyl, 2-(β-cyanoethyl)-propyl, ω-cyanoheptyl and ω-cyanooctyl.

The following are examples of phenyl groups substituted by an alkyl radical: tolyl, ethyl, phenyl, propyl-phenyl, n-butylphenyl, tert.-butylphenyl, di-tert.-butyl-phenyl and tri-tert.-butylphenyl.

The following are examples of alkyl radicals substituted by a phenyl radical: phenylmethyl, phenylethyl, phenylpropyl, phenyl-tert.-butyl and ω-phenylhexyl.

The following oxirane compounds are mentioned by way of example:
2,3-dimethyloxirane, 2-methyl-3-ethyloxirane, 2-methyloxirane, 2-ethyloxirane, 2-n-butyloxirane, 2-isobutyloxirane, 2-tert.-butyloxirane, 2-phenyloxirane, 2-pentyloxirane, 2,3-diethyloxirane, 2,3-dihexyloxirane, 2-ethyl-3-hexyloxirane, 2,3-di-octyloxirane, 2-(2-ethyl)-hexyl-3-methyloxirane, 2-nonyl-3-methyloxirane, 2,3-diisopropyloxirane, 2,3-diundecyloxirane, 2,3-didodecyloxirane, 2-pentadecyl-3-hexyloxirane, 2-hexadecyl-3-octadecyloxirane, 2-(β-ethylbutyl)-3-(α-ethylbutyl)-oxirane, 2,3-di-(3-pentylhexyl)-oxirane, 2-chloromethyloxirane, 2-(β-chloroethyl)-oxirane 3-(γ-chloropropyl)-oxirane, 2-chloromethyl-3-methyloxirane, 2,3-di-chloroxirane, 2,3-di(β-chloroethyl)-oxirane, 2,3-di-(γ-chloropropyl)-oxirane, 2,3-di(α-chloro-n-butyl)-oxirane, 2-fluoromethyloxirane, 2,3-trifluoromethyloxirane, 2,3-di-(β-hydroxyethyl)-oxirane, 2,3-di(γ-hydroxypropyl)-oxirane, 2,3-dimethoxyoxirane, 2,3-di-(β-methoxyethyl)-oxirane, 2-(γ-propoxypropyl)-3-propyloxirane, 2,3-di(β-hexoxyethyl)-oxirane, 2,3-di-(carbomethoxymethyl)-oxirane, 2,3-dicarbomethoxy-oxirane, 2,3-di-(carboisopropoxymethyl)-oxirane, 2,3-di-(β-cyanoethyl)-oxirane, 2,3-di-(β-phenylethyl)-oxirane, phenyloxirane, 2,3-diphenyloxirane, 2,3-di-(p-chlorophenyl)-oxirane, 2,3-di-(p-fluorophenyl)-oxirane, 2,3-di-(2,4-dichlorophenyl)-oxirane, 2,3-di-(4-bromo-3,5-di-tert.-butylphenyl)-oxirane, 2,3-di-(4-cyanophenyl)-oxirane, 2,3-di-(4-methoxyphenyl)-oxirane, 2,3-di-(2,4-isopropoxyphenyl)-oxirane, 2,3-di-(4-hexoxyphenyl)-oxirane, 2,3-di-(2,4-dimethylphenyl)-oxirane, 2,3-di-(4-tert.-butylphenyl)-oxirane, 2-(4-oxiranylphenyl)-oxirane, 2-(2-oxiranylphenyl)-oxirane, 2-(oxiranylmethyl)-oxirane, 2-(β-oxiranylethyl)-oxirane, cyclobutyloxirane, 2,3-dicyclobutyloxirane, 2,3-dicyclopentyloxirane, 2,3-dicyclohexyloxirane, cyclohexyloxirane, 2-cyclohexyl-3-methyloxirane, 2,3-di-(α-chlorocyclohexyl)-oxirane, 2,3-di(α-methyloxycyclopentyl)-oxirane, 2,3-di-(β-propoxycyclohexyl)-oxirane, 2,3-di-(α-carboisopropoxycyclopentyl)oxirane, 2,3-di-(α-cyanocyclododecenyl)-oxirane, α-cyancyclopentyloxirane, β-cyanocyclopentyloxirane, 2,3-di-(β-cyanocyclohexyl)- oxirane, 2,3-di(β-fluorocyclohexyl)-oxirane, 2,3-di-(trifluoromethylcyclohexyl)-oxirane, (4-oxiranylcyclohexyl)oxirane and (3-oxiranylcyclopentyl)-oxirane.

Another preferred group of compounds within the scope of general formula (I) corresponds to the formula (II)

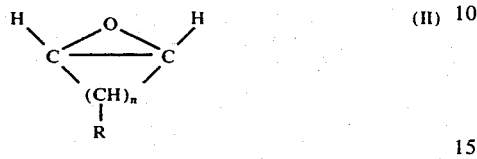

in which n is an integer from 3 to 5 and each of the C-atoms defined by n can be substituted by R independently of one another when R represents fluorine, chlorine, cyanide, $C_1-C_6$-alkoxy, $C_1-C_6$-alkyl, $C_5-C_7$-cycloalkyl or a phenyl group optionally substituted by fluorine, chlorine, cyanide or $C_1-C_6$-alkoxy.

The following are mentioned in particular: cyclopentene-1,2-oxide, 3-chlorocyclopentene-1,2-oxide, 3,5-dichlorocyclopentene-1,2-oxide, 4-hydroxycyclopentent-1,2-oxide, 3,5-dimethylcyclopentene-1,2-oxide, 3,5-diethylcyclopentene-1,2-oxide, 4-isopropylcyclopentene-1,2-oxide, 4-tert.-butylcyclopentene-1,2-oxide, 3,5-diphenylcyclopentene-1,2-oxide, 3,5-di-(4-chlorophenyl)-cyclopentene-1,2-oxide, 4-phenylcyclopentene-1,2-oxide, 3-methoxycyclopentene-1,2-oxide, 4-propoxycyclopentene-1,2-oxide, 3,5-diisopropoxycyclopentene-1,2-oxide, 4-tert.-butoxycyclopentene-1,2-oxide, 4-n-hexoxycyclopentene-1,2-oxide, 3-carbomethoxycyclopentene-1,2-oxide, 4-carbopropoxycyclopentene-1,2-oxide, 3,5-di-[(β-caromethoxy)-ethyl]-cyclopentene-1,2-oxide, 3-cyanocyclopentene-1,2-oxide, 4-cyanocyclopentene oxide, 4-(β-cyanoethyl)-cyclopentene-1,2-oxide, 3-fluorocyclopentene-1,2-oxide, 3-trifluoromethylcyclopentene-1,2-oxide, cyclohexene oxide, 3-fluorocyclohexene-1,2-oxide, 3-trifulouromethylcyclohexene-1,2-oxide, 3-chlorocyclohexene-1,2-oxide, 4-chlorocyclohexene-1,2-oxide 5-chlorocyclohexene-1,2-oxide, 4,5-dichlorocyclohexene-1,2-oxide, 3-hydroxycyclohexene-1,2-oxide, 3,6-dihydroxycyclohexene-1,2-oxide, 3-methylcyclohexene-1,2-oxide, 4-methylcyclohexene-1,2-oxide, 5-ethylcyclohexene-1,2-oxide, 3,5-diisopropylcyclohexene-1,2-oxide, 4,5-diphenylcyclohexene-1,2-oxide, 4-phenyl cyclohexene-1,2-oxide, 4,5-diphenylcyclohexene-1,2-oxide, 4-(p-chlorophenyl)-cyclohexene-1,2-oxide. 3-methoxycyclohexene-1,2-oxide, 4-ethoxycyclohexene-1,2-oxide, 4-isopropoxycyclohexene-1,2-oxide, 4-hexoxycyclohexene-1,2-oxide (4-(β-cyanoethyl)-cyclohexene-1,2-oxide, cycloheptenoxide, 3-methylcycloheptene-1,2-oxide, 3,7-dimethylcycloheptene-1,2-oxide, 4,5,6-trimethylcycloheptene-1,2-oxide, 5-isopropyl cycloheptene-1,2-oxide, 5-tert.-butylcycloheptene-1,2-oxide, 3-chlorocycloheptene-oxide, 4-(β-chloroethyl)-cycloheptene-1,2-oxide, 4,6-dichlorocycloheptene-1,2-oxide, 5-hydroxycycloheptene-1,2-oxide, 4,6-dihydroxycycloheptene-1,2-oxide, 3-phenylcycloheptene-1,2-oxide, 5-phenylcycloheptene-1,2-oxide, 4,6-di-(p-tert.-butylphenyl)-cycloheptene-1,2-oxide, 3-methoxycycloheptene-1,2-oxide, 5-methoxycycloheptene-1,2-oxide, 3-propoxycycloheptene-1,2-oxide, 5-tert.-butoxycycloheptene-1,2-oxide, 3-carbomethoxycycloheptene-1,2-oxide, 4-carbomethoxycycloheptene-1,2-oxide, 3,7-dicarbomethoxycycloheptene-1,2-oxide, 5-(β-carbomethoxy)-ethylcycloheptene-1,2-oxide.

In the process according to the present invention, the oxirane compound is split with ring opening, 2 molecules of aldehyde being formed per molecule of oxirane compounds. One exception are those oxirane compounds in which $R_1$ together with $R_2$ forms a cycloalkyl radical according to general formula I above. In this case ring opening is accompanied by the formation of a dialdehyde. Thus, in the process according to the present invention one molecule of acetaldehyde and 1 mol of propionaldehyde are obtained, for example from 1 mol of pentene-2,3-oxide, and 2 mols of acetaldehyde from butene-2,3-oxide, whereas glutardialdehyde is obtained from cyclopentene oxide and adipic aldehyde from cyclohexene oxide.

It is not essential to start directly from the oxirane compounds; instead, it is also possible to react oxirane compounds formed in situ by known reactions in accordance with the invention.

Suitable compounds of boron include boron oxides, boric acids, salts and esters of boric acids, boron-halogen compounds, boron phosphates and complex boron compounds.

The following are mentioned as examples of boric acids: orthoboric acid, metaboric acid and tetreboric acid. Suitable salts include the alkali and alkaline earth salts of these acids, and their zinc and aluminium salts. The following salts are mentioned by way of example:

Sodium orthoborate, sodium metaborate, sodium tetraborate, lithium orthoborate, lithium metaborate, lithium tetraborate, potassium orthoborate, potassium metaborate, potassium tetraborate, magnesium orthoborate, magnesium metaborate, magnesium tetraborate, calcium orthoborate, calcium metaborate, calcium tetraborate, zinc orthoborate, zinc metaborate, zinc tetraborate, aluminium orthoborate, aluminium metaborate and aluminium tetraborate.

Suitable boric acid esters are compounds corresponding to the general formula III:

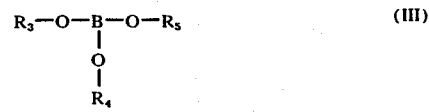

in which $R_3$, $R_4$ and $R_5$ independently of one another represent a $C_1-C_6$-alkyl group optionally substituted by hydroxyl, fluorine, chlorine, $C_1-C_3$-alkoxy or phenyl; a $C_5-C_7$-cycloalkyl group or a phenyl group optionally substituted by fluorine, chlorine or $C_1-C_3$-alkyl.

The following are mentioned as examples of $R_3$, $R_4$ and $R_5$.

Chloromethyl, hydroxymethyl, β-hydroxymethyl, β-methoxyethyl, 3-propoxypropyl, toluene, ethylphenyl, propylphenyl and tert.-butylphenyl.

The following are mentioned as examples of boric acid esters:

Boric acid trimethyl ester, boric acid triethyl ester, boric acid tri-n-hexyl ester, boric acid tricyclohexyl ester, boric acid tri-(β-methoxyethyl)-ester, boric acid tri-(β-fluoroethyl)-ester, boric acid triphenylester, boric acid tri-(p-chlorophenyl)-ester, boric acid tri-(p-methoxyphenyl)-ester and boric acid tri-(β-hydroxyethyl)-ester.

Boron trifluoride and boron trichloride are mentioned as representatives of halogen compounds of boron. Suitable complex boron compounds are compounds which represent adducts of alcohols of the general formula $R_3$—OH, of alcoholates of the general formula $R_3$—OMe, of ethers corresponding to the general formula $R_3$—O—$R_4$, of carboxylic acids corresponding to the general formula $R_3$—COOH or of hydrogen halide, with compounds of the general formula III, boron trifluoride or boron trichloride, $R_3$ and $R_4$ having the same meaning as in general formula III whilst Me in the case of the alcoholates can represent the alkali and alkaline-earth metals, zinc or aluminium. The following are mentioned as examples of complex boron compounds:

Tetramethoxy boric acid, lithium tetramethoxy borate, sodium tetramethoxy borate, magnesium ditetramethoxy borate, zinc ditetramethoxy borate, boron trifluoride diethyl etherate, boron trifluoride trimethyl etherate, boron trifluoride acetic acid, boron trifluoride propionic acid, tetrafluorboric acid, sodium trimethoxy monocyclohexyloxy borate.

Boric acid anhydride can also be added.

The quantity in which the boron compound is added can be varied within wide limits, small quantities being sufficient. In general, the boron compound will be added in a quantity of less than 20 mol percent, based on the quantity of hydrogen peroxide used, quantities of from 0.01 to 10 mol percent being preferred. The boron compound can be either soluble or insoluble in the reaction mixture. The boron compound can also be applied to inert supports for example aluminium oxide, aluminium oxide hydrate, silica gel or zeolites, and used in this form.

The process according to the invention is generally carried out by adding the oxirane compound with stirring to a mixture of hydrogen peroxide and boron compound or, conversely, by initially introducing the oxirane compound and the boron compound and subsequently adding hydrogen peroxide with stirring. The reaction is carried out in suitable reactors known per se. Allowance must be made, as known per se, for the catalytic effects of the wall and for the influence of foreign ions entering the solution through corrosion.

It is preferred to use hydrogen peroxide in the form of non-aqueous solutions. Compounds which neither react with the oxirane compound used nor cause decomposition of the hydrogen peroxide are used as solvents for hydrogen peroxide. Non-aqueous hydrogen peroxide solutions of this kind are obtained, for example, in accordance with DAS No. 1,802,003. Also these non-aqueous solutions can be obtained by adding a solvent miscible with water and hydrogen peroxide to an aqueous hydrogen peroxide solution and subsequently removing the water, preferably by distillation in vacuo. Solvents suitable for this purpose are in particular esters, N-alkyl-substituted acid amides, alcohols, carboxylic acids, sulphonic acids and phosphoric acids. The esters and alkylamides of the phosphoric acids, phosphonic acids and phosphinic acids are particularly suitable, the following being mentioned by way of example: triethyl phosphate, methane phosphonic acid dimethyl ester, β- cyanoethylphosphonic acid dimethyl ester, β-carbomethoxyphosphonic acid methyl ester, trioctyl phosphate and trihexyl phosphate.

Another embodiment of the process according to the invention uses solvent mixtures which afford advantages over the use of a single solvent in regard to their dissolving properties for the simultaneous dissolution of hydrogen peroxide, boron compound, olefin oxide and the aldehydes formed. These advantages are reflected in the fact that it is possible to start with a more highly concentrated parent solution of hydrogen peroxide in a phosphonic acid ester for example a 30% solution of hydrogen peroxide in methane phosphonic acid dimethyl ester, and to add to the solution an inert solvent such as ethyl acetate, butyl acetate or methylene chloride, thereby increasing the solubility of the boron compound and of the oxirane compound to be used.

The concentration of the non-aqueous hydrogen peroxide solutions used can fluctuate within wide limits and in practice is determined solely by the explosion limits. Accordingly, the upper limit to the hydrogen peroxide concentration will be between 30 and 60%, depending upon the solvent used. In general, the hydrogen peroxide is used in a concentration of from 3 to 30%, the use of non-aqueous solutions of hydrogen peroxide with a concentration of from 10 to 20% being preferred.

The molar ratio of the oxirane compound to hydrogen peroxide in the starting solution can vary within wide limits. However, it is advantageous, if the hydrogen peroxide used is to be completely reacted, to use an excess of oxirane compound of generally from 10 to 500 percent and preferably from 15 to 100 percent.

The temperature at which the process according to the invention is carried out is essentially governed by the stability of the hydrogen peroxide in the corresponding reaction mixture. As a rule, the limits are determined by the decomposition temperature of the pure hydrogen peroxide. In general, the process is carried out at a temperature in the range from $-80°$ to $+120°C.$, and preferably from $+20$ to $+80°C.$ The pressure is determined by the vapour pressure of the reactants and of the solvent used and accordingly can vary within wide limits. It has no critical effect upon the reaction. The process according to the invention can be carried out both in the gaseous phase and in the liquid phase.

The reaction time differs according to the oxirane compound used, the reaction temperature and the boron compound added. However, it is generally very short. Thus, the reaction is generally substantially over after the reactants have been mixed and can be completed simply by stirring the reaction mixture. In some cases, the aldehyde does not immediately exist completely as such. In such cases, it is best to reheat the reaction mixture to an elevated temperature, for example, to around $80°$ to $100°C.$, on completion of the reaction. The addition of acids, for example sulphuric acid, hydrochloric acid or hydrofluoric acid, has an accelerating effect.

The aldehydes are isolated by methods known per se, for example by ordinary distillation or steam distillation. It can be advantageous to remove the aldehyde from the reaction mixture by extraction, for example in the case of water soluble aldehydes by extraction with water. The further processing of aqueous phases obtained in this way is known per se. It can also be advantageous, before working up the reaction mixture, temporarily to convert the aldehyde group into other functional groups. Of the known possibilities, reference is only made here to conversion into the acetals.

EXAMPLE 1 a. 15.1 g of cyclopentene oxide were gradually added dropwise with stirring at 35°C. to a mixture of 45.79 g of a 10.95 solution of hydrogen peroxide in triisooctyl phosphate and 0.2 g of boron trifluoride diethyl etherate, measures being adopted to ensure that the temperature does not exceed +20°C.

After 3 hours, the reaction mixture had a glutardialdehyde content of 18.96% according to analysis by gas chromatography in a 2 m-column with 5% of nitrile silicone on silanised, acid-washed kieselguhr with cyclohexyl acetate as internal standard.

The reaction mixture was extracted with 50 g of boiling hot water. A 12% aqueous solution of glutardialdehyde was obtained in this way.

b. 50 g of reaction mixture prepared in accordance with (a) containing 18.96% of glutardialdehyde, were heated to boiling point with 50 g of water over a period of 10 minutes. Thereafter both phases were separated. 40.5 g of an upper phase containing 2.14 g of glutardialdehyde and 59.5 g of an aqueous phase containing 7.11 g of glutardialdehyde were obtained in this way. The upper phase was re-extracted with 40 g of water, this time in the absence of heat. Two phases were obtained, the upper phase containing 0.60 g of glutardialdehyde and the lower aqueous phase 1.50 g of glutardialdehyde.

The glutardialdehyde content was determined both by gas chromatography and in conventional manner by reacting the glutardialdehyde obtained with hydroxylammonium hydrochloride and titrating the hydrocyloric acid liberated.

EXAMPLE 2

15.1 g of cyclopentene oxide were added with stirring at 40°C. to a mixture of 44.4 g of an 11.26% solution of hydrogen peroxide in triisooctyl phosphate and 0.5 g of boric acid anhydride. After 4 hours, the mixture had the following composition according to analysis by gas chromatography:

| | |
|---|---|
| Glutardialdehyde: | 15.35% |
| Trans-cyclo-1,2-hexane diol: | 0.46% |
| Cyclopentene oxide: | 7.92% |

The excess cyclopentene oxide was removed as known per se by vacuum distillation and the residual mixture extracted with 50 g of water. A 10% aqueous solution of glutardialdehyde was thus obtained.

EXAMPLE 3

15.1 g of cyclopentene oxide were added with stirring at 40°C. to a mixture of 51.99 g of a 9.26% hydrogen peroxide solution in triisooctyl phosphate and 1.0 g of boric acid trimethyl ester.

The reaction mixture had the following composition according to analysis by gas chromatography.

| | |
|---|---|
| Glutardialdehyde: | 7.44% (5.07 g) |
| Cyclopentene oxide: | 15.05% (10.25 g) |

EXAMPLE 4

15.1 g of cyclopentene oxide were gradually added at 0°C. to a mixture of 51.91 g of a 9.63% solution of hydrogen peroxide in tributyl phosphate and 0.2 g of boron fluoride acetic acid. After 4 hours, analysis of the reaction mixture by gas chromatography produced the following results:

| | |
|---|---|
| Cyclopentene oxide: | 7.35% (4.95 g) |
| Glutardialdehyde: | 15.26% (10.29 g) |

After the excess cyclopentene oxide had been removed as known per se by vacuum distillation, a 12% aqueous solution of glutardialdehyde was obtained by extracting the reaction mixture with 50 g of boiling hot water.

EXAMPLE 5

15.1 g of cyclopentene oxide were added with stirring at 15°C. to a mixture of 77.0 g of a 6.5% solution of hydrogen peroxide in isoamylacetate and 0.2 of boron trifluoride etherate. After 3 hours, the reaction mixture had the following composition according to analysis by gas chromatography:

| | |
|---|---|
| Glutardialdehyde: | 11.72% (10.8 g) |
| Cyclopentene oxide: | 3.15% (2.9 g) |

EXAMPLE 6

17.9 g of cyclohexene oxide were gradually added to a mixture of 46.6 g of a 10.73% solution of hydrogen peroxide in triisooctylphosphate and 0.2 g of boron trifluoride ethyl dietherate. After 4 hours, analysis of the reaction mixture by gas chromatography showed that it contained 15.48% (9.8 g) of adipic dialdehyde.

EXAMPLE 7

16.2 g of butene-2,3-oxide were added with stirring at 15°C. to a mixture of 46.6 g of a 10.5% solution of hydrogen peroxide in triisooctylphosphate and 0.2 g of boron trifluoridediethyl etherate.

After 3 hours, the reaction mixture had an acetic aldehyde content of 16.0 % (10,05 g).

EXAMPLE 8

21.6 g of styrene oxide were added dropwise with stirring at 15°C. to a mixture of 46.6 g of a 10.5% solution of hydrogen peroxide in triisooctylphosphate and 0.2 g of boron trifluoride etherate.

After 2 hours, the reaction mixture was found by gas-chromatographic analysis to contain 10.95% (7.5 g) of benzaldehyde and 2.9% (1.98 g) of formaldehyde.

What is claimed is:

1. Process for producing dialdehydes which comprises reacting an oxirane compound having the formula:

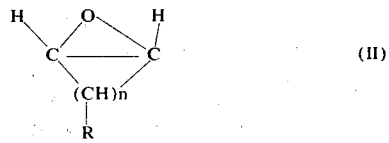

wherein n is an integer from 3 to 5 and each of the carbon atoms defined by n can be substituted by R independently of one another, where R is selected from the group of fluorine, chlorine, cyanide, $C_1$–$C_6$-alkoxy, $C_1$–$C_6$-alkyl, $C_5$–$C_7$-cycloalkyl, and phenyl optionally substituted by fluorine, chlorine, cyanide or $C_1$-$C_6$-alkoxy, with non-aqueous hydrogen peroxide in a solvent that does not react with the oxirane compound nor cause decomposition of the hydrogen peroxide, at a temperature of from −80° to 120°C in the presence of a boron compound selected from the group of a boron oxide, a boric acid, boric acid anhydride and a boric acid ester having the formula

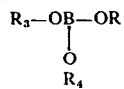

wherein $R_3$, $R_4$ and $R_5$ independently of one another are selected from the group of $C_1$-$C_6$-alkyl, $C_5$-$C_7$-cycloalkyl and phenyl, said boron compound being present in a quantity of up to 20 mol percent based on the hydrogen peroxide.

2. Process of claim 1, wherein the oxirane compound is cyclopentene-1,2-oxide or cyclohexene-1,2-oxide.

3. Process of claim 1 wherein the boron compound is boric acid trimethyl ester.

4. Process of claim 1 wherein a solvent selected from the group of an alcohol, carboxylic acid, ester, acid amide, and hydrocarbon substituted by fluorine or chlorine is used as the solvent for hydrogen peroxide.

5. Process of claim 1 wherein an ester or an alkyl amide of a phosphoric acid, phosphonic acid or phosphinic acid is used as the solvent for hydrogen peroxide.

6. Process of claim 1 wherein a non-aqueous solution of hydrogen peroxide in tributyl phosphate, trioctyl phosphate or isoamyl acetate is used.

7. Process of claim 1 wherein the boron compound is present in a quantity of from 0.01 to 10 mol percent.

8. Process of claim 1 wherein the reaction is carried out at a temperature of from +20° to +80°C.

* * * * *

UNITED STATES PATENT AND TRADEMARK OFFICE
CERTIFICATE OF CORRECTION

PATENT NO. : 3,974,224
DATED : August 10, 1976
INVENTOR(S) : Helmut Waldmann et al It is certified that error appears in the above–identified patent and that said Letters Patent are hereby corrected as shown below:

Col. 2, line 64, "meth[yl]oxycyclopentyl" should read

-- methoxycyclopentyl --

Col. 2, line 67, "cyancyclopentyloxirane" should read

-- cyanocyclopentyloxirane --

Col. 9, line 11, "R$_3$--OB--OR" should read

-- R$_3$—OB—OR$_5$ --.

Signed and Sealed this

Eighteenth Day of January 1977

[SEAL]

Attest:

RUTH C. MASON
Attesting Officer

C. MARSHALL DANN
Commissioner of Patents and Trademarks